United States Patent [19]
Barcay et al.

[11] Patent Number: 5,820,855
[45] Date of Patent: Oct. 13, 1998

[54] WATER POWDER AS A SYNERGIST IN PEST BAITS

[75] Inventors: Stephen John Barcay, Burnsville; Douglas G. Anderson, Lakeville, both of Minn.

[73] Assignee: Ecolab Inc., St. Paul, Minn.

[21] Appl. No.: 261,986

[22] Filed: Jun. 17, 1994

[51] Int. Cl.$^6$ .......................... A01N 59/14; A01N 25/00; A01N 25/12; A01N 25/26
[52] U.S. Cl. .......................... 424/84; 424/400; 424/405; 424/406; 424/409; 424/410; 424/417; 424/420; 424/484; 424/659; 426/1; 514/547; 514/772; 514/785; 514/786; 514/951
[58] Field of Search .............................. 424/84, 400, 405, 424/406, 409, 410, 417, 420, 484, 659; 426/1; 514/547, 772, 785, 786, 951

[56] References Cited

U.S. PATENT DOCUMENTS

| | | | |
|---|---|---|---|
| 3,887,710 | 6/1975 | Shaver et al. | 424/300 |
| 4,696,822 | 9/1987 | Matsumura et al. | 424/490 |
| 4,759,930 | 7/1988 | Granirer | 424/195.1 |
| 4,889,710 | 12/1989 | Hagarty | 424/45 |
| 5,104,658 | 4/1992 | Hagarty | 424/405 |
| 5,116,618 | 5/1992 | Hagarty | 424/405 |
| 5,464,613 | 11/1995 | Barcay et al. | 424/84 |
| 5,480,638 | 1/1996 | Erwin | 424/84 |
| 5,575,996 | 11/1996 | Erwin | 424/84 |

FOREIGN PATENT DOCUMENTS

| | | |
|---|---|---|
| 57-203001 | 12/1982 | Japan . |
| WO 91/07972 | 6/1991 | WIPO . |

OTHER PUBLICATIONS

Technical Data, Kerry Ingredients, Item No. TBD, Entrapped water powder Oct. 5, 1992.
Arthur G. Appel, *Laboratory and Field Performance of Consumer Bait Products for German Cockroach* (Dictyopters: Blattellidae) *Control,* Entomological Society of America 1990, pp. 153–159.
Arthur G. Appel, *Performance of Gel and Paste Bait Products for German Cockroach* (Dictyoptera: Blattellida) *Control: Laboratory and Field Studies,* Entomological Society of America, vol. 85, No. 4, Aug. 1992, pp. 1176–1183.
Michael K. Rust, "Managing Household Pests", *Advances in Urban Pest Management,* G.W. Bennet and M. Owens (eds), Van Nostrand Reinhold, New York 1986, pp. 335–368.
William H. Robinson, *Proceedings of the National Conference on Urban Entomology,* 1992, pp. 77–91.
Michael K. Rust et al., *Attraction and Performance of Insecticidal Baits for German Cockroach Control,* International Pest Control 1981, pp. 106–109.
Farm Chemicals Handbook '87, Meister Publishing Co., Ohio, 1987, p. C102, see the entry under "Dusts".

*Primary Examiner*—John Pak
*Attorney, Agent, or Firm*—Merchant, Gould, Smith, Edell, Welter & Schmidt

[57] ABSTRACT

Novel insecticidal compositions are described which are particularly effective against insect pests such as cockroaches, ants, termites, crickets, flies and the like, which contain an effective amount of insecticide and a synergistic effective amount of water powder. The compositions, preferably using boric acid as an insecticide, and preferably in the form of a paste or dust bait, kill such pests more quickly or allow lower concentrations of insecticide to be used in such compositions.

16 Claims, 2 Drawing Sheets

WATER POWDER AS A SYNERGIST IN PEST BAITS

FIELD OF THE INVENTION

This invention relates to the use of water powder in insecticide bait formulations for controlling insects such as, for example, cockroaches, ants, termites, crickets, flies and the like.

BACKGROUND OF THE INVENTION

Generally, the process for manufacturing water powder or entrapped water is known but the material is not used commercially. Chemical attractants and feeding stimulants have been known to enhance the efficacy of insect bait by increasing the attraction to or increasing the ingestion rate of insect baits. Water powder is neither an attractant nor a feed stimulant, but surprisingly it synergizes bait active ingredients. By adding water powder to insect bait formulations, there is a significant increase in the speed or rate of kill of insects as compared to baits without water powder, or the same rate of kill is observed by using lower amounts of active ingredient when mixed with water powder.

SUMMARY OF THE INVENTION

Accordingly, the present invention is an insecticide composition for use against insect pests comprising an effective amount of insecticide and a synergistic effective amount of water powder.

A particular aspect of the present invention is an insecticide composition for use against insect pests comprising an effective amount of boric acid and at least 5 wt. % of water powder.

Another aspect of the present invention is an insecticide composition for use against insect pests comprising: about 5–60 wt. % boric acid and about 5–50 wt. % of water powder.

Still another aspect of the present invention is a method of controlling insect pests comprising applying to areas to be controlled an insecticide composition comprising an effective amount of insecticide and a synergistic effective amount of water powder.

DETAILED DESCRIPTION OF THE INVENTION

Figure 1:
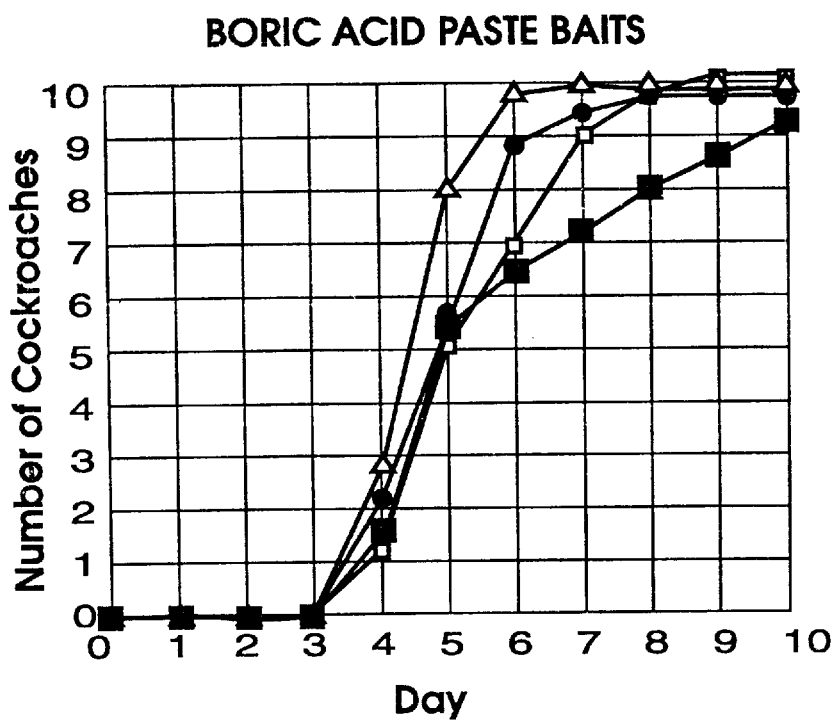
FIG. 1 is a plot of the percent kill of cockroaches over a ten day period with a boric acid paste bait formulation with and without water powder.

The baits of the present invention are preferably used in the form of a paste or dust. These formulations may be further modified by well known manufacturing methods into various other types of forms and textures depending on the targeted insect, such as, for example, granules, pellets and the like. The use of the composition is designed against a wide variety of insects, including, but not limited to cockroaches, ants, crickets, termites, flies and the like.

An essential ingredient of the present invention is the presence of water powder in a synergistic effective amount. Since water powder per se has no insecticidal activity, any increase in killing action or the faster onset of killing action by the addition of water powder to an insecticide over the known rate of kill of the insecticide is deemed to provide a synergistic effect. Such synergistic effective amount will vary depending on the choice of insecticide and the targeted pest. As a preferred embodiment, at least about 5 wt. % water powder is used, especially, for example, when boric acid is the insecticide.

As an example, water powder or otherwise known as entrapped water powder, may be purchased from Kerry Food Ingredients, Beloit, Wis., whose product is composed of approximately 30.0 wt. % water, 70.0 wt. % hydrogenated soybean oil. The Kerry water powder is a white powder, free from hard lumps and has a 100% pass through a #12 U.S. Standard Sieve. Water powder, however, may vary in composition since it is by definition any water entrapped in a solid fat. Thus in the manufacture of a water powder product, water powder may contain materials that are water-soluble or capable of forming aqueous suspensions. For example, the water powder may also contain monoglycerides, sorbic acid and salts thereof, such as, for example, potassium sorbate, and lactic acid. In addition, the water powder may optionally contain the insecticide of choice, as defined below, or known chemical synergists, as defined below, alone or in combination with the insecticide. This is especially the case when the insecticide is other than boric acid and can be effective at amounts as low as about 0.001 wt. %. The water powder may optionally further include other agents which will enhance the killing power of the insecticide composition, for example sorbitol. The above aqueous solution or suspension is entrapped into fat and is released after ingestion and digestion by the insect. Thus, the use of water powder in conjunction with an insecticide will reduce the amount of insecticide needed for efficacy and increase the rate of kill of the active ingredient. At the normal amount used in a formulation, the water powder will synergize the effect of the insecticide.

The fat component in water powder is a solid fat and preferably hydrogenated soybean oil. However, the fat component may include those defined below as a fat-based carrier, preferably in solid form.

Since the present invention is directed to the concept of using water powder in a bait formulation, this composition can include any insecticide. Included as examples of active ingredients are compounds from the following classes of insecticides:

1 -organophosphates, e.g. acephate, chlorpyrifos or diazinon;

2-mineral acids, e.g. boric acid;

3-carbamates, e.g. propoxur, 2-(1,3-dioxolane-2-yl)-phenyl-N-methylcarbamate, or o-isopropoxy-phenylmethyl-carbamate;

4-pyrethroids, e.g. cyfluthrin;

5-amidinohydrazones, e.g. hydramethylnon;

6-avermectins, e.g. abamectin;

7-chlorinated hydrocarbons, e.g. lindane, and combinations of the above with known synergists, e.g. o-isopropoxy-phenylmethyl-carbamate or 2-(1,3-dioxolane-2-yl)-phenyl-N-methylcarbamate may be combined with piperonyl butoxide or piperonal bis-(2,2-butoxyethoxy)-ethyl)acetal. The most preferred insecticide of the present invention is boric acid.

The insecticidal composition of the present invention may contain a carrier which is an excipient or diluent. As an example of an acceptable carrier for the water-powder insecticide composition, one may add a fat-based carrier which contains a fat or mixtures thereof. By definition a fat is "A glycerol ester of fatty acid(s): Fats generally are substances of plant and animal origin. Fat may be in a solid form, as tallow, lard, butter, margarine or other shortenings or in liquid form, e.g., as vegetable oils." Certain vegetable oils can also be solid depending on the degree of hydrogenation or saturation.

The glycerol esters are predominantly of the triglyceride type, vegetable oils and fats may also contain some di- and even mono-glycerides. Fatty acid component of fats and vegetable oils encompass the range of fatty acids containing from about 8–22 carbon atoms, primarily in a range of C12 and C18. Although most of the fatty acid content is saturated linear alkanoic acid, some of the fatty acid content may be unsaturated, as exemplified by oleic and linoleic acid. Examples of preferred fats and oils used in the present invention are partially hydrogenated vegetable oil comprising soybean and cottonseed oil mixtures in solid or liquid flake form, partially hydrogenated cottonseed oil in solid form, partially hydrogenated soybean oil in solid form, partially hydrogenated vegetable oil containing a mixture of palm kernel and coconut oils in liquid form, partially hydrogenated coconut oil in liquid plastic form, partially hydrogenated vegetable oil in liquid flake form comprising a mixture of a palm kernel and cottonseed with lecithin, hydrogenated cottonseed oil, hydrogenated palm oil, hydrogenated soybean oil, hydrogenated vegetable oil in liquid form containing a mixture of rapeseed, cottonseed and soybean oil, partially hydrogenated vegetable oil containing a mixture of soybean and palm oil with vegetable mono and diglycerides, in plastic form, partially hydrogenated vegetable oil containing soybean, cottonseed with vegetable mono and diglycerides in plastic form, partially hydrogenated vegetable oil in paste or margarine type of form which contains a mixture of soybean and cottonseed oils with water, salt, nonfat milk, lecithin, mono and diglycerides, sodium benzoate, artificial color, artificial flavor, vitamin A palmitate, soybean oil, corn oil, coconut oil, mono and diglycerides, ethoxylated mono and diglycerides, polyglycerol esters of fatty acids, and polyglycerol as fatty acids.

The insecticidal composition of the present invention may also contain, if desired, preservatives, flowing agents, and the like. The composition may further contain attractants and feeding stimulants depending on the targeted insect. Such feeding stimulants are for example, carbohydrates, carbohydrate complexes, carbohydrates, e.g., maltodextrins and the like, carbohydrate complexes, e.g., corn syrup solids, protein such as yeast extracts, milk solids, sugars such as sucrose, glucose, fructose, starches such as corn, potato and the like. Examples of attractants are odorants and flavorants such as for example cyclotenes and the like, plant extracts such as fenugreek and the like, alcohols such as ethanol, or a combination of ethanol with a volatile ester. Such volatile ester is prepared from a combination of a $C_1$–$C_6$ branched or unbranched alcohol and a $C_1$–$C_3$ carboxylic acid. Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof, etc. Carboxylic acids useful in manufacturing the ester attractant of the invention include acetic acid, propionic acid, butyric acid, mixtures thereof, and others. The associated reactive analogs of the respective carboxylic acids can be used, for example, the acid chloride or acid anhydride. The preferred volatile ester for use in this invention is a lower alcohol acetate ester such as n-amyl acetate, isoamyl acetate, isobutyl acetate, n-propyl acetate, ethyl acetate or mixtures thereof. Some of the ingredients may overlap in category as they can be both attractants and feed stimulants, for example proteins mentioned above, and odorants and flavorants. Examples of preservatives are butylated hydroxy toluene (BHT) and the like. Examples of flowing agents are silica and the like.

Preferred embodiments of the present invention include the composition in a form of a paste or dust and comprise an effective amount of insecticide and at least 5 wt. % water powder.

A preferred boric acid composition comprises about 5–60 wt. % boric acid, and about 5–50 wt. % water powder.

As an example of a boric acid and water powder bait formulation, the following ranges are representative for the compositions:

5.0–60 wt. % boric acid
10–50 wt. % water powder
5–50.0 wt. % hydrogenated soybean oil
20.0–50.0 wt. % soybean oil
1.0–20.0 wt. % sucrose
0.02–0.1 wt. % BHT (preservative)
1.0–25.0 wt. % yeast extract
0.1–1.0 wt. % fenugreek extract
1.0–5.0 wt. % silica (flowing agent)

With the exception of the water powder and the boric acid active ingredient, one or all of the remaining ingredients can be present in the formulation but are optional only. Other inert ingredients known in the art to enhance the palatability of bait formulations may also be utilized depending on the targeted insects.

More preferred boric acid compositions comprise about 40 to 60 wt. % boric acid and about 10–50 wt. % water powder.

As an example of the use of the present invention, inclusion of water powder in boric acid bait formulations has been found to significantly increase the speed of kill from these baits. This has been shown for both dust and paste formulations of boric acid bait, FIGS. 1 and 2.

As a paste or dust, the above described compositions can be used in containerized or non-containerized bait traps or preferably applied in cracks and crevices of apartments, homes or industrial settings where pests, especially cockroaches and ants are likely to reside. Pastes and dusts are applied in and around cracks and crevices, for example, in the kitchens and bathrooms of the above structures for effective control and killing of these pests. Pastes and dusts can be manufactured by well-known methods which essentially comprise blending the active insecticide and water powder with a carrier. Additional ingredients, if desired, are also added during the blending operation.

The following examples are used to illustrate the present invention but are not limited thereon.

EXAMPLE 1

Boric Acid Paste Bait

The following ingredients were blended into a paste:

45.0 wt. % boric acid
7.5 wt. % sucrose
7.4 wt. % corn syrup solids
28.0 wt. % soybean oil
11.9 wt. % entrapped water powder
0.1 wt. % fenugreek extract
0.1 wt. % butylated hydroxy toluene (BHT)

EXAMPLE 2

Dust Boric Acid Dust Bait

The following materials were blended:

60.0 wt. % boric acid
12.0 wt. % water powder
3 wt. % silica (flowing agent)
12.5 wt. % sucrose
12.5 wt. % yeast extract

EXAMPLE 3

Methods for Bait Evaluations

Choice tests were performed against German cockroaches for the purpose of evaluating toxic bait efficacy. German cockroach adult males were placed into jars and provided with food and water. The jars were greased around the upper lip with petrolatum to prevent escape. After a four hour acclimation period, cockroaches were presented with a bait. In these tests, cockroaches were allowed to choose between an alternative food source (Purina Dog Chow) and the bait tested. Cockroaches were exposed to the boric acid baits continuously during the test period. Observations of bait attractiveness, palatability, and daily mortality after exposure to the bait were recorded. There were four replications of each treatment.

The following boric acid paste baits were formulated to compare a formulation containing 15% water powder and a formulation of boric acid without water powder. The results are shown in FIG. 1 which demonstrates the superior kill of cockroaches with the formulations containing the water powder.

| A | B |
|---|---|
| 45.0 wt % boric acid | 47.0 wt % boric acid |
| 15.0 wt % water powder | 15.0 wt % sucrose |
| 15.0 wt % sucrose | 5.0 wt % flour |
| 25.0 wt % soybean oil | 25.0 wt % soy shortening |
|  | 8.0 wt % water |

"The two additional water powder formulations in FIG. 1 were prepared as in A above."

EXAMPLE 4

Figure 2:
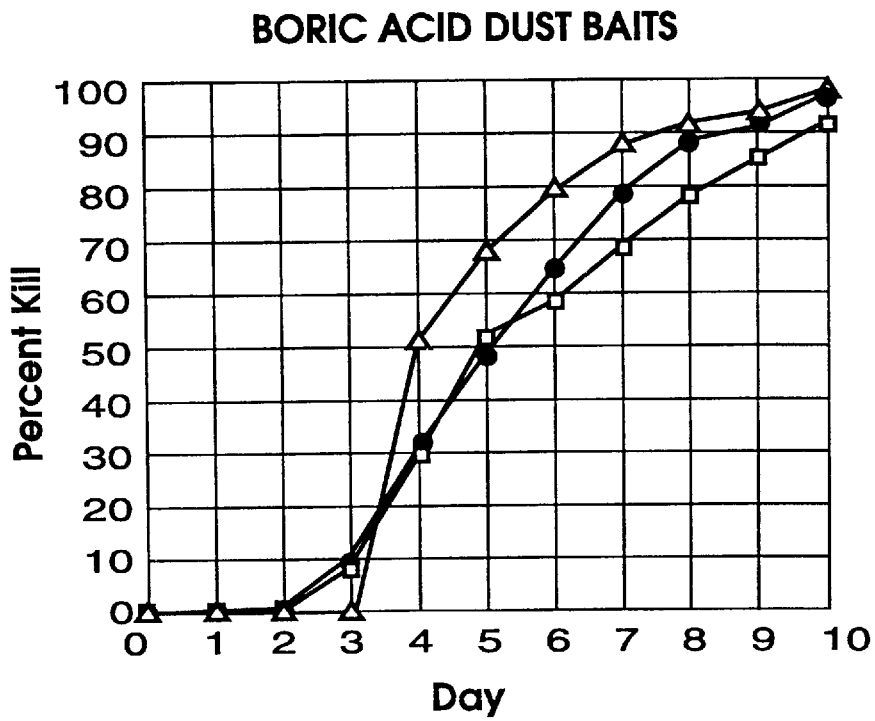
FIG. 2 is a plot of the percent kill of cockroaches over a ten day period comparing a boric acid dust bait formulation with and without water powder.

The following boric acid dust baits were formulated to determine the percent kill of cockroaches over a ten day period as reported in FIG. 2. One formulation contained 15 wt. % water powder whereas the other two contained no water powder. The percentage kill of cockroaches was significantly faster for the water powder composition, sample C, over the composition absent water powder, sample D. For example, a 50% kill was observed on day 4 for sample C, over a 30% kill for sample D.

| C | D |
|---|---|
| 45.0 wt % boric acid | 45.0 wt % boric acid |
| 15.0 wt % water powder | 25.0 wt % sucrose |
| 15.0 wt % sucrose | 30.0 wt % yeast extract |
| 25.0 wt % yeast extract |  |

"The additional no water powder formulation in FIG. 2 containing 50% boric acid was prepared as in D above."

What is claimed is:

1. An insecticidal composition for use against insect pests comprising an effective amount of boric acid and a synergistic effective amount of water powder comprising water and partially hydrogenated soybean oil.

2. A composition according to claim 1, containing at least 5 wt. % water powder.

3. An insecticidal composition for use against insect pests comprising: about 5–60 wt. % boric acid and about 5–50 wt. % of water powder comprising water and partially hydrogenated soybean oil.

4. The composition of claim 3 in the form of a paste.

5. The composition of claim 3 in the form of a dust.

6. An insecticidal composition for use against insect pests comprising:

about 40–60 wt. % boric acid, and at least 10–50 wt. % of water powder comprising water and partially hydrogenated soybean oil.

7. The composition of claim 6 in the form of a paste.

8. The composition of claim 6 in the form of a dust.

9. A method of controlling insect pests comprising applying to areas to be controlled an insecticidal composition comprising an effective amount of boric acid and a synergistic effective amount of water powder comprising water and partially hydrogenated soybean oil.

10. The method of claim 9, wherein at least 5 wt. % water powder is used.

11. The method of claim 9, wherein the composition comprises:

about 5–60 wt. % boric acid, and about 5–50 wt. % of water powder.

12. The method of claim 9, wherein the composition comprises:

about 40–60 wt. % of boric acid, and about 10–50 wt. % water powder.

13. The method of claim 9, wherein the composition is in the form of a paste.

14. The method of claim 9, wherein the composition is in the form of a dust.

15. An insecticidal composition for use against insect pests comprising an effective amount of boric acid and a synergistic effective amount of water entrapped in a solid fat in particulate form dispersed in a carrier.

16. The composition of claim 15 wherein the carrier is fat-based.

* * * * *